US012629538B2

(12) United States Patent
Dijkstra

(10) Patent No.: US 12,629,538 B2
(45) Date of Patent: May 19, 2026

(54) WEARABLE PHOTOTHERAPY DEVICE

(71) Applicant: SHENZHEN KAIYAN MEDICAL EQUIPMENT CO., LTD, Shenzhen (CN)

(72) Inventor: Alain Dijkstra, Amstelveen (NL)

(73) Assignee: Shenzhen Kaiyan Medical Equipment Co., Ltd, Shenzhen (CN)

( * ) Notice: Subject to any disclaimer, the term of this patent is extended or adjusted under 35 U.S.C. 154(b) by 555 days.

(21) Appl. No.: 18/295,861

(22) Filed: Apr. 5, 2023

(65) Prior Publication Data

US 2024/0261587 A1    Aug. 8, 2024

(30) Foreign Application Priority Data

Feb. 8, 2023    (CN) .......................... 202320152848.0

(51) Int. Cl.
| | |
|---|---|
| *A61N 5/06* | (2006.01) |
| *A61N 1/20* | (2006.01) |
| *A61N 1/30* | (2006.01) |
| *A61N 1/36* | (2006.01) |
| *A61N 1/40* | (2006.01) |

(52) U.S. Cl.
CPC ........... *A61N 5/0616* (2013.01); *A61N 1/205* (2013.01); *A61N 1/303* (2013.01); *A61N 1/36003* (2013.01); *A61N 1/36021* (2013.01); *A61N 1/403* (2013.01); *A61N 2005/0626* (2013.01); *A61N 2005/0647* (2013.01); *A61N 2005/0652* (2013.01); *A61N 2005/0659* (2013.01); *A61N 2005/066* (2013.01); *A61N 2005/0662* (2013.01)

(58) Field of Classification Search
CPC ...... A61N 5/0616; A61N 1/205; A61N 1/303; A61N 1/36003; A61N 1/36021; A61N 1/403; A61N 1/0484; A61N 2005/0626; A61N 2005/0647; A61N 2005/0652; A61N 2005/0659; A61N 2005/066; A61N 2005/0662; A61N 2005/0645; A61N 2005/0663
See application file for complete search history.

(56) References Cited

U.S. PATENT DOCUMENTS

| | | | |
|---|---|---|---|
| 2007/0276318 A1 | 11/2007 | Henley | |
| 2010/0241056 A1* | 9/2010 | Lehtoluoto | A61N 1/328 |
| | | | 604/20 |
| 2012/0172940 A1* | 7/2012 | Wahls | A61N 1/0476 |
| | | | 607/3 |
| 2017/0246445 A1* | 8/2017 | Planard-Luong | A61N 1/327 |
| 2021/0162209 A1 | 6/2021 | Chen | |
| 2022/0080221 A1* | 3/2022 | Gross | A61N 5/0616 |
| 2022/0257971 A1* | 8/2022 | Kim | A61M 37/00 |
| 2022/0339462 A1* | 10/2022 | Bhardwaj | A61N 5/0616 |
| 2023/0000683 A1* | 1/2023 | Kang | A61N 1/04 |

* cited by examiner

*Primary Examiner* — Ankit D Tejani
*Assistant Examiner* — Joshua Brendon Solomon
(74) *Attorney, Agent, or Firm* — Willie Jacques; Emanus LLC

(57) ABSTRACT

A wearable phototherapy device comprises an outer layer, an inner transparent silicone layer, a plurality of light sources located between the outer layer and the inner transparent silicone layer, wherein the plurality of light sources is directed towards the inner transparent silicone layer, and a metallic layer printed onto an inner surface of the inner transparent silicone layer, wherein the metallic layer is configured to conduct electrical current.

19 Claims, 6 Drawing Sheets

WEARABLE PHOTOTHERAPY DEVICE

TECHNICAL FIELD

The present invention generally relates to therapeutic devices. More specifically the present invention relates to light or electromagnetic radiation-based therapeutic devices.

BACKGROUND ART

Light therapy devices have been known in the art for quite a while. Many such devices are designed to be wearable in nature such as in the shape of a face mask, an armband, or a belt for the waist region. Such devices in construction generally have an outer layer and a transparent inner layer and several LEDs located between the outer layer and the transparent inner layer. The LEDs have been located in such a manner that the LEDs are directed toward the inner transparent layer. In many such devices, the LEDs, in whole or in part, may be replaced with other light sources such as, but not limited to, halogen lamps or LASERs. In general, light sources, either LEDs or other light sources such as halogen lamps and LASERs, emit radiation between the infrared and ultraviolet ends of the electromagnetic spectrum. The aim of such devices is to impart irradiation to a specific body part of the user to cause skin regeneration and repair as the skin absorbs photons from the irradiation and enhances the production of Adenosine Tri-Phosphate (ATP) and collagen.

However such devices have the singular functionality of providing light therapy and are not able to combine other therapies, such as Transcutaneous Electrical Nerve Stimulation (TENS), Electronic Muscle Stimulation (EMS), and Radio-Frequency (RF) with light therapy. Phototherapy, however, alone may not be as effective, especially in the case of applications such as wound healing or pain relief. In such scenarios and also to enhance skin regeneration in general, a combination of therapies may be required to achieve optimal results. As a result, a user needs to purchase multiple devices each providing a different therapy. This adds to cost and complexity on the part of the user as purchasing multiple devices contributes to added costs and changing between the multiple devices contributes to the complexity of the operation.

Therefore, there is a need for a device that overcomes the disadvantages and limitations associated with the prior art and provides a more satisfactory solution.

OBJECTS OF THE INVENTION

Some of the objects of the invention are as follows:

An object of the invention is to provide a wearable phototherapy device that includes a printed metallic layer that is electrically conductive.

Another object of the invention is to provide a wearable phototherapy device that also includes several metal electrodes interspersed along the metallic layer.

Another object of the invention is to provide a wearable phototherapy device that is capable of providing multiple therapies such as Transcutaneous Electrical Nerve Stimulation (TENS), Electronic Muscle Stimulation (EMS), Galvanic Therapy, Radio-Frequency (RF), etc.

Another object of the invention is to provide a wearable phototherapy device where the metallic layer has been provided in predetermined patterns.

Yet another object of the invention is to provide a wearable phototherapy device that that can take several forms such as a face mask, an armband, a belt, etc.

SUMMARY OF THE INVENTION

According to a first aspect of the present invention, there is provided a wearable phototherapy device, the wearable phototherapy device comprising an outer layer, an inner transparent silicone layer, a plurality of light sources located between the outer layer and the inner transparent silicone layer, wherein the plurality of light sources is directed towards the inner transparent silicone layer, and a metallic layer printed onto an inner surface of the inner transparent silicone layer, wherein the metallic layer is configured to conduct electrical current.

In one embodiment of the invention, the wearable phototherapy device further comprises a plurality of metal electrodes interspersed along the metallic layer.

In one embodiment of the invention, the plurality of metal electrodes are floating electrodes.

In one embodiment of the invention, the plurality of metal electrodes is configured to transmit electrical current within the metallic layer.

In one embodiment of the invention, a plurality of regions of the metallic layer between the interspersed plurality of metal electrodes correspond to a plurality of parts of the body of a user.

In one embodiment of the invention, the flow of current to the plurality of regions is configured to be individually controlled through control of the flow of current to individual metal electrodes of the plurality of metal electrodes.

In one embodiment of the invention, the plurality of metal electrodes is configured to emit Radio-Frequency (RF) waves to provide RF treatment to the body of a user.

In one embodiment of the invention, the plurality of metal electrodes are supported by elastic members at the points of attachment of the plurality of metal electrodes.

In one embodiment of the invention, the wearable phototherapy device is in the shape of a face mask.

In one embodiment of the invention, the metallic layer has been provided in the form of a pattern including a plurality of connected hexagons.

In one embodiment of the invention, the plurality of light sources includes Light Emitting Diodes (LEDs).

In one embodiment of the invention, the plurality of light sources is configured to emit radiation in visible light and infrared wavelengths of the electromagnetic spectrum.

In one embodiment of the invention, the metallic layer is configured to conduct electrical current to provide Galvanic therapy to a user, the Galvanic therapy including desincrustation and iontophoresis.

In one embodiment of the invention, the metallic layer is configured to conduct electrical current to provide Transcutaneous Electrical Nerve Stimulation (TENS) to a user.

In one embodiment of the invention, the metallic layer is configured to conduct electrical current to provide Electronic Muscle Stimulation (EMS) to a user.

In one embodiment of the invention, the wearable phototherapy device further comprises a battery, a control unit, and a mode controller.

In one embodiment of the invention, the control unit is configured to connect with an external communication device and receive an input from the external communication device.

In one embodiment of the invention, the inner transparent silicone layer includes a plurality of holes for the plurality of light sources and acts as a spacer between the metallic layer and the plurality of light sources.

In one embodiment of the invention, the plurality of metal electrodes are used to provide iontophoresis therapy.

In one embodiment of the invention, the plurality of metal electrodes are used to provide therapies including Electronic Muscle Stimulation (EMS), and Transcutaneous Electrical Nerve Stimulation (TENS).

In the context of the specification, the phrase "Transcutaneous Electrical Nerve Stimulation (TENS)" refers to electrical stimulation of muscles with low voltage electrical current using electrical electrodes for pain relief. The electrodes are placed at or near the nerves where the pain is located or at trigger points.

In the context of the specification, the phrase "Electronic Muscle Stimulation (EMS)" refers to electrical stimulation of specific muscle groups with a current of slightly greater magnitude than used in TENS to achieve muscle contractions. EMS can be used to enhance muscle strength, reduce swelling, relieve pain and help heal wounds.

In the context of the specification, the phrase "Galvanic Therapy" refers to application of direct current to the epidermis of a patient. The Galvanic Therapy aims to achieve a myriad of skin benefits like softening tissue, and softening blackheads by dilating the pores, stimulating cells, and driving ingredients deep into the epidermis. The Galvanic Therapy is of two types, desincrustation, and iontophoresis. Desincrustation includes the application of a desincrustation solution and then the movement of an active electrode to the area to be treated. Iontophoresis includes the application of galvanic current on the positive polarity. During an iontophoresis treatment, a product that has an acidic pH and is water-soluble can be used. Gels, serums, or even a mask can be applied all over the area to be treated. Moreover, an inactive (negative) electrode is placed on other parts of the body of the patient, such as under their shoulder, while a positive current is delivered into the skin via positively charged ions.

In the context of the specification, the phrase "Radio Frequency (RF) Treatment" refers to the application of RF waves to the dermis layer of a patient to generate heat, using a handheld probe. The handheld probe is applied topically on the upper layers of the skin as the RF waves penetrate deep into the skin, upto the dermis layer. The treatment aims to enhance the production of collagen and elastin for skin regeneration and growth.

In the context of the specification, the term "processor" refers to one or more of microprocessors, a microcontroller, a general-purpose processor, a Field Programmable Gate Array (FPGA) or an Application Specific Integrated Circuit (ASIC), and the like.

In the context of the specification, the phrase "storage memory" refers to one or more of a volatile storage memory, such as Static Random Access Memory (SRAM) and Dynamic Random Access Memory (DRAM) of types such as Asynchronous DRAM, Synchronous DRAM, Double Data Rate SDRAM, Rambus DRAM, and Cache DRAM, etc., or a non-volatile storage memory such as EPROM, EEPROM or flash memory or the like.

In the context of the specification, the phrase "communication interface" refers to a device or a module enabling direct connectivity via wires and connectors such as USB, HDMI, VGA, or wireless connectivity such as Bluetooth or Wi-Fi or Local Area Network (LAN) or Wide Area Network (WAN) implemented through TCP/IP, IEEE 802.x, GSM, CDMA, LTE or other equivalent protocols.

In the context of the specification, the term "historical" in execution of a command refers to anything pertaining to a time instant(s) that is earlier than a time instant of an initiation of the command.

In the context of the specification, the term, "real-time", refers to without intentional delay, given the processing limitations of hardware/software/firmware involved and the time required to accurately measure/receive/process/transmit data as practically possible.

In the context of this specification, terms like "light", "radiation", "irradiation", "emission" and "illumination", etc. refer to electromagnetic radiation in wavelength ranges varying from the visible light wavelengths (380-700 nm) to Infrared (IR) wavelengths (780 nm-1 mm), wherein the range is inclusive of visible light and IR wavelengths. The IR radiation may also be categorized into several categories according to respective wavelength ranges which are again envisaged to be within the scope of this invention. A commonly used subdivision scheme for IR radiation includes Near IR (0.75-1.4 μm), Short-Wavelength IR (1.4-3 μm), Mid-Wavelength IR (3-8 μm), Long-Wavelength IR (8-15 μm) and Far IR (15-1000 μm).

In the context of the specification, a "polymer" is a material made up of long chains of organic molecules (having eight or more organic molecules) including, but not limited to, carbon, nitrogen, oxygen, and hydrogen as their constituent elements. The term polymer is envisaged to include both naturally occurring polymers such as wool, and synthetic polymers such as polyethylene and nylon.

In the context of the specification, "Light Emitting Diodes (LEDs)" are envisaged to be characterized by their superior power efficiencies, smaller sizes, rapidity in switching, physical robustness, and longevity when compared with incandescent or fluorescent lamps. In that regard, the plurality of LEDs may be through-hole type LEDs (generally used to produce electromagnetic radiations of red, green, yellow, blue and white colors), Surface Mount LEDs, Bi-color LEDs, Pulse Width Modulated RGB (Red-Green-Blue) LEDs, Organic LEDs (OLEDs) and high-power LEDs, etc.

Materials used in the one or more LEDs may vary from one embodiment to another depending upon the frequency of radiation required. Different frequencies can be obtained from LEDs made from pure or doped semiconductor materials. Commonly used semiconductor materials include nitrides of Silicon, Gallium, Aluminum, and Boron, and Zinc Selenide, etc. in pure form or doped with elements such as Aluminum and Indium, etc. For example, red and amber colors are produced from Aluminum Indium Gallium Phosphide (AlGaInP) based compositions, while blue, green, and cyan use Indium Gallium Nitride based compositions. White light may be produced by mixing red, green, and blue lights in equal proportions, while varying proportions may be used for generating a wider color gamut. White and other colored lightings may also be produced using phosphor coatings such as Yttrium Aluminum Garnet (YAG) in combination with a blue LED to generate white light and Magnesium doped potassium fluorosilicate in combination with blue LED to generate red light. Additionally, near Ultraviolet (UV) LEDs may be combined with europium-based phosphors to generate red and blue lights and copper and zinc doped zinc sulfide-based phosphor to generate green light.

In addition to conventional mineral-based LEDs, one or more LEDs may also be provided on an Organic LED (OLED) based flexible panel or an inorganic LED-based flexible panel. Such OLED panels may be generated by depositing organic semiconducting materials over Thin Film Transistor (TFT) based substrates. Further, discussion on generation of OLED panels can be found in Bardsley, J. N (2004), "*International OLED Technology Roadmap*", *IEEE Journal of Selected Topics in Quantum Electronics, Vol.* 10, *No.* 1, that is included herein in its entirety, by reference. An exemplary description of flexible inorganic light-emitting diode strips can be found in granted U.S. Pat. No. 7,476,557 B2, titled "Roll-to-roll fabricated light sheet and encapsulated semiconductor circuit devices", which is included herein in its entirety, by reference.

In several embodiments, the one or more LEDs may also be micro-LEDs described through U.S. Pat. Nos. 8,809,126 B2, 8,846,457 B2, 8,852,467 B2, 8,415,879 B2, 8,877,101 B2, 9,018,833 B2 and their respective family members, assigned to NthDegree Technologies Worldwide Inc., which are included herein by reference, in their entirety. The one or more LEDs, in that regard, may be provided as a printable composition of the micro-LEDs, printed on a substrate.

BRIEF DESCRIPTION OF THE ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

DETAILED DESCRIPTION

Figure 1:
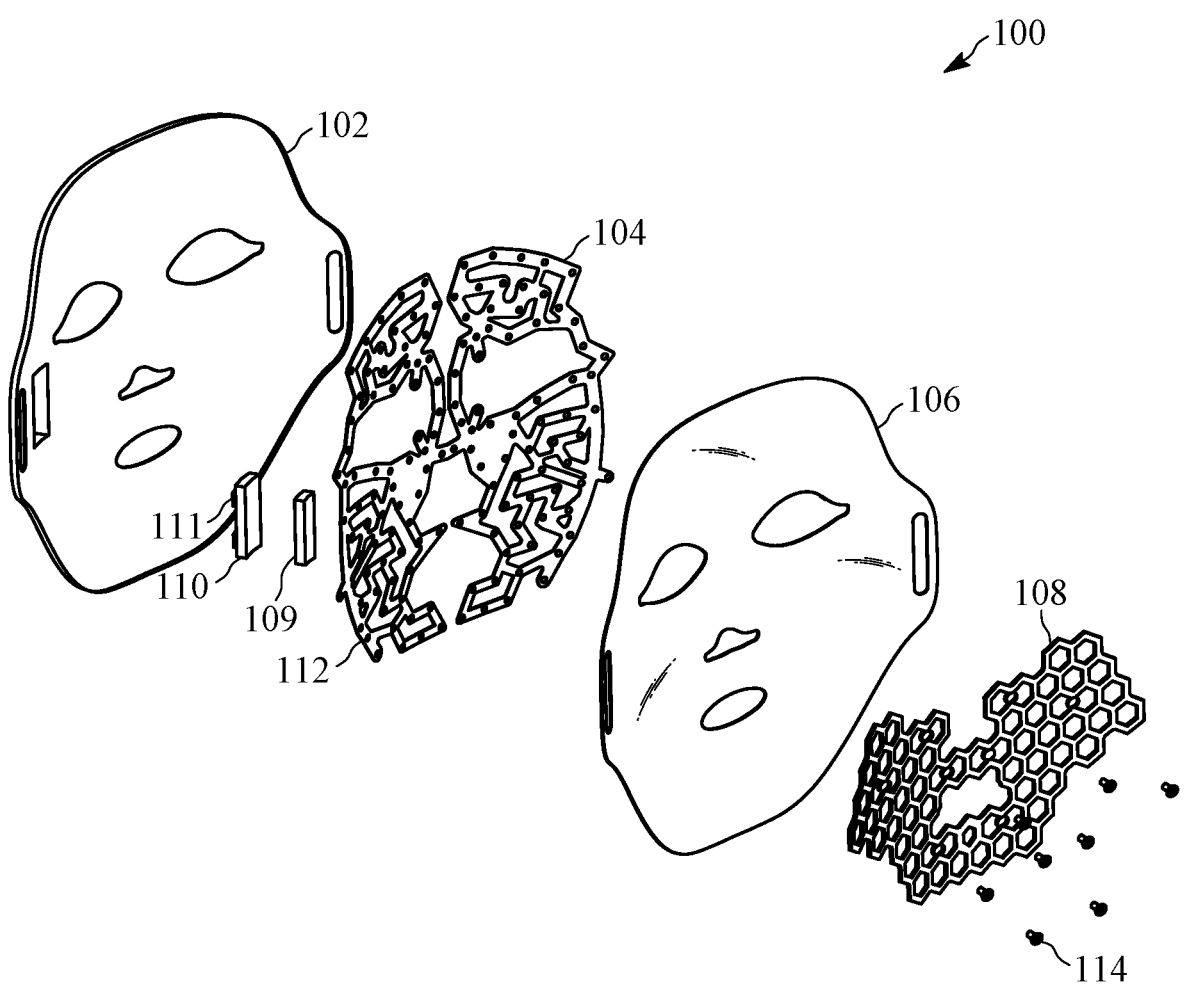
FIG. 1 illustrates an exploded view of a wearable phototherapy device in accordance with an embodiment of the present invention.

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure. The following detailed description is therefore not to be taken in a limiting sense, and the scope of the present invention disclosure is defined by the appended claims. Embodiments of the claims may, however, be embodied in many different forms and should not be construed as limited to the embodiments set forth herein.

It is envisaged that a wearable phototherapy device is provided that provides several alternative treatments to a user along with light therapy. Such alternative treatments may include Transcutaneous Electrical Nerve Stimulation (TENS), Electronic Muscle Stimulation (EMS), Radio-Frequency (RF), Galvanic therapy, etc. To that end, a metallic layer has been provided on an inner transparent layer of the device, in a manner that the metallic layer conducts electricity and makes contact with the skin of the user. The alternative treatments are achieved through the flow of electrical current in the metallic layer. To enhance the effectiveness of the metallic layer, several metal electrodes have been interspersed along the metallic layer. The metal electrodes form several regions that may be individually controlled through control of the flow of current to individual metal electrodes. Further, the wearable phototherapy device may take the shape of a face mask, an armband, a waist belt, etc. Referring to the drawings, the invention will now be explained in further detail.

Figure 2:
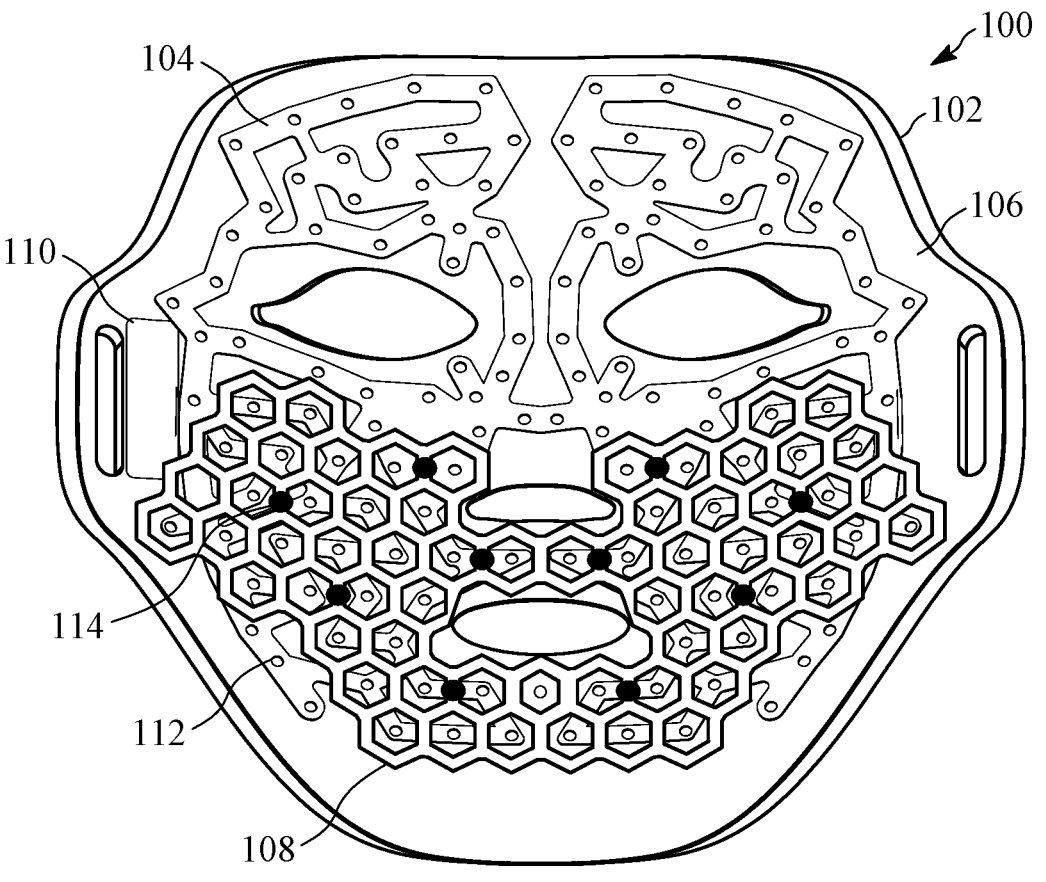
FIG. 2 illustrates a rear perspective view of the wearable phototherapy device, in accordance with an embodiment

FIG. 1 illustrates an exploded view of a wearable phototherapy device 100 (hereinafter referred to as "the device 100") in accordance with an embodiment of the present invention. FIG. 2 illustrates a rear perspective view of the device 100, in accordance with an embodiment. As illustrated in FIGS. 1 and 2, the device 100 is in the shape of a face mask. However, in several alternate embodiments, the device 100 may take several other forms, such as an armband, a jacket, or a waist belt. The device 100 includes an outer layer 102 and an inner transparent layer 106. In several embodiments of the invention, the inner transparent layer 106 is made up of silicone material, alternatively the inner transparent layer is made of Methyl Methacrylate Cross polymer silicone to shine the face more efficiently and enhances the light therapy effect. A plurality of light sources 112 is located between the outer layer 102 and the inner transparent layer 106. The plurality of light sources 112 have been provided on a flexible Printed Circuit Board (PCB) 104 and is directed towards the inner transparent layer 106. The inner transparent layer 106 further includes holes for fixing the plurality of light sources 112. Moreover, the inner transparent layer 106 creates a gap between the plurality of light sources 112 and a metallic layer 108. The gap will further illuminate the treatment area and diffuse the light from the plurality of light sources 112 to provide a better therapeutic effect. In several embodiments of the invention, the plurality of light sources 112 includes Light Emitting Diodes (LEDs). In several embodiments of the invention, the plurality of light sources 112 is configured to emit radiation in red and infrared frequencies of the electromagnetic spectrum.

Further, the metallic layer 108 has been printed onto an inner surface of the inner transparent layer 106. The metallic layer 108 is configured to conduct electrical current. In several embodiments of the invention, the metallic layer 108 has been provided in the form of a pattern including a plurality of connected hexagons. In several embodiments of the invention, the metallic layer 108 is configured to conduct electrical current to provide Transcutaneous Electrical Nerve Stimulation (TENS) to a user. In several alternate embodiments, the metallic layer 108 is configured to conduct electrical current to provide Electronic Muscle Stimulation (EMS) to a user. In several embodiments of the invention, the device 100 also includes a plurality of metal electrodes 114 interspersed along the metallic layer 108.

Figure 3:
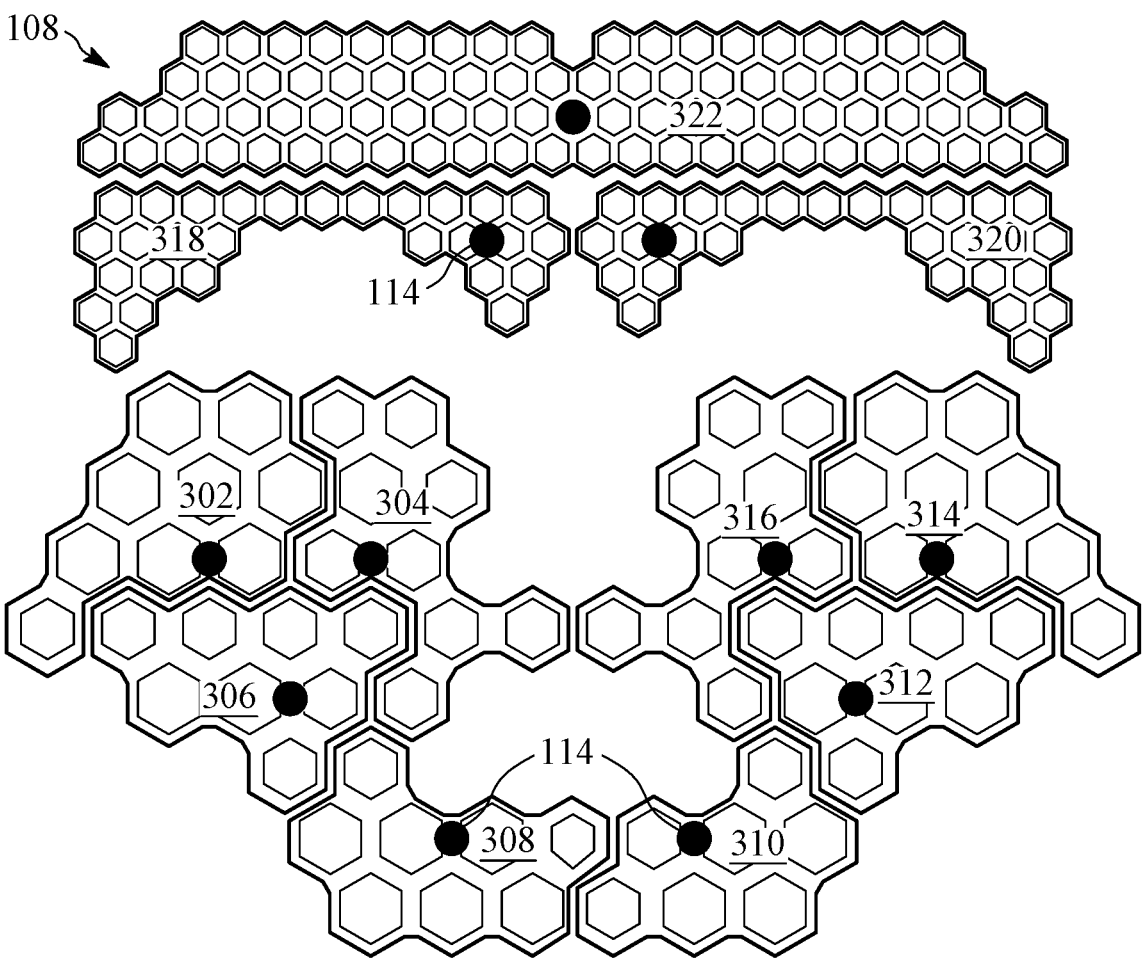
FIG. 3 illustrates a metallic layer with interspersed metal electrodes, in accordance with an embodiment of the present invention.

FIG. 3 illustrates the metallic layer 108 with the interspersed plurality of metal electrodes 114, in accordance with an embodiment of the present invention. The plurality of metal electrodes 114 is configured to transmit electrical current within the metallic layer 108. The plurality of metal electrodes 114 divides the metallic layer 108 into a plurality of regions 302, 304, 306, 308, 310, 312, 314, 316, 318, 320 and 322. The plurality of regions 302, 304, 306, 308, 310, 312, 314, 316, 318, 320 and 322 may then correspond to a plurality of parts of the body of a user. For example, if the device 100 is in shape of a face mask, then one region 304 may correspond to upper jaw region, another region 302 may correspond to area surrounding the eye and yet another region 306 may correspond to cheek of the user. In this manner, the whole face of the user may receive electrical stimulation from the plurality of metal electrodes 114 and the metallic layer 108. Also, the plurality of regions 302, 304, 306, 308, 310, 312, 314, 316, 318, 320 and 322 are disconnected from each other.

In that manner, the flow of current to the plurality of regions 302, 304, 306, 308, 310, 312, 314, 316, 318, 320 and 322 may be configured to be individually controlled through control of the flow of current to individual metal electrodes of the plurality of metal electrodes 114. In that regard, the flow of current to the area surrounding the eyes, the upper jaw, and the cheek of the user may be controlled through control of the flow of current to the individual electrodes, thereby providing an option for directed and selective treatment of specific part of the body of the user. The application of TENS, EMS and Galvanic Therapy also may be directed to specific part of the body of the user. Another advantage of the plurality of metal electrodes 114 is that they can be used to provide Radio Frequency (RF) treatment. Through electromagnetic interactions, the plurality of metal electrodes 114 may be configured to emit Radio-Frequency (RF) waves to provide RF treatment to the body of a user. In one embodiment of the invention, the plurality of metal electrodes 114 are also configured to balance the pH level of the contact area through electrolysis. In one embodiment of the invention, the plurality of metal electrodes 114 are floating electrodes. In several embodiments of the invention, the metallic layer 108 and the plurality of metal electrodes 114 are configured to conduct electrical current to provide Galvanic therapy to a user, the Galvanic therapy including desincrustation and iontophoresis.

Desincrustation involves the application of an alkaline solution with negatively charged ions to an affected area. The alkaline desincrustation solution is applied to both the skin and the gauze or cotton covering the active electrode, which traditionally is a prong or a tweezer, this is then moved over the affected area. In the current embodiment, the plurality of metal electrodes 114 and the metallic layer 108 act as the active electrodes by connecting them with a negative terminal of a power source such as a battery. For example, when the device 100 is in the form of a face mask, the desincrustation solution is applied to the skin of the face of a user and then the device 100 is applied to the face of the user. The negative ions in the solution are repelled by the plurality of metal electrodes 114 and the metallic layer 108, causing an alkaline reaction in the skin. This works on the theory that like poles repel and opposite poles attract. The alkaline desincrustation solution, combined with the action of the active negative electrode, results in the "saponification" of sebum. This alkali and sebum reaction forms sodium hydroxide (lye) due to the fatty stearic acids in sebum, reacting with the alkali to form soap. In the skin, the reaction softens and liquefies sebum, and this facilitates the easier release of blackheads.

Iontophoresis involves active transdermal drug delivery involving delivery of drug ions through the skin using low level electric current. When Direct Current (DC) is applied to an ionized drug solution, ions that have same charge as the current are repelled by the current and delivered through the skin. For example, the ionized drug solution may be applied to the face of the user, and the device 100 is embodied as an facemask. The DC current is applied through the metallic layer 108 and the plurality of metal electrodes 114. The ions in the drug solution are repelled and absorbed through the face of the user and provide skin enhancement effect to the user. Iontophoresis can be used with water soluble ionic medications to treat acute tendonitis, pain associated with calcific deposits, and provide dermal anesthesia. Iontophoresis has several advantages over alternatives of injections and oral medications. Iontophoresis is virtually painless and is non-invasive minimizing the risk of infection and tissue necrosis and tendon rupture.

Figure 4A:
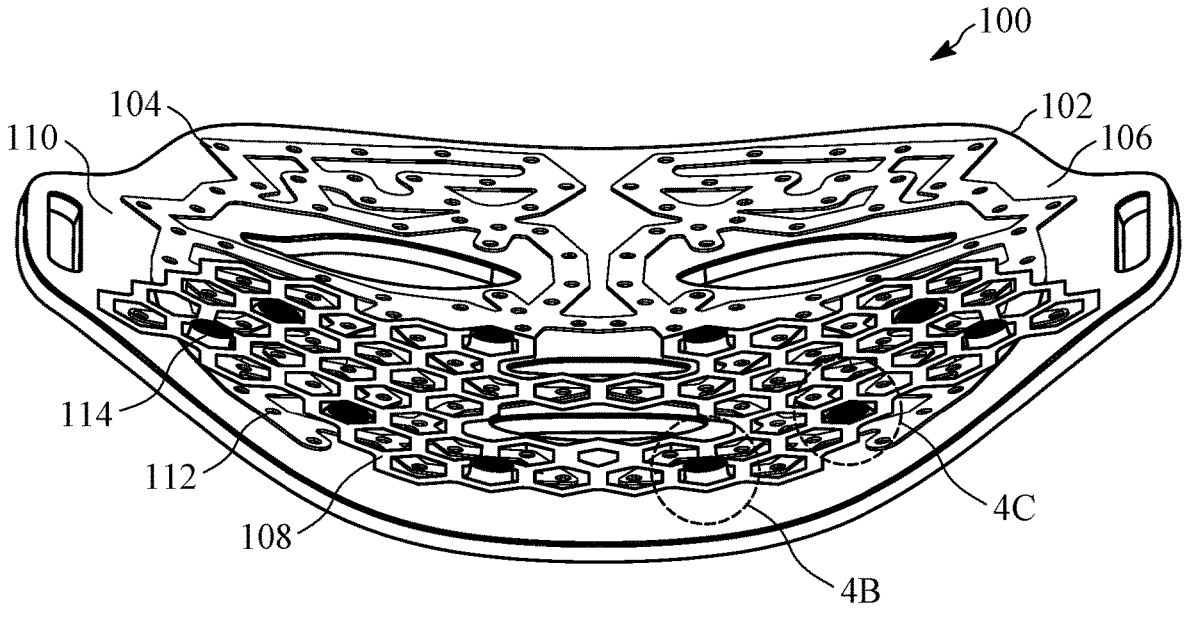
FIG. 4A illustrates a bottom perspective view of the wearable phototherapy device, in accordance with an embodiment of the present invention.

FIG. 4A illustrates a bottom perspective view of the device 100. The bottom perspective view illustrates the outer layer 102, the flexible circuit board 104, the inner transparent layer 106, the metallic layer 108, the control unit 110, the plurality of light sources 112, and the plurality of metal electrodes 114 as described in the aforementioned description. It is further envisaged that the plurality of metal electrodes 114 are floating electrodes. In that regard, the plurality of metal electrodes 114 adapt to the shape of a portion of the body on which the device 100 has been worn.

Figures 4B, 4C:
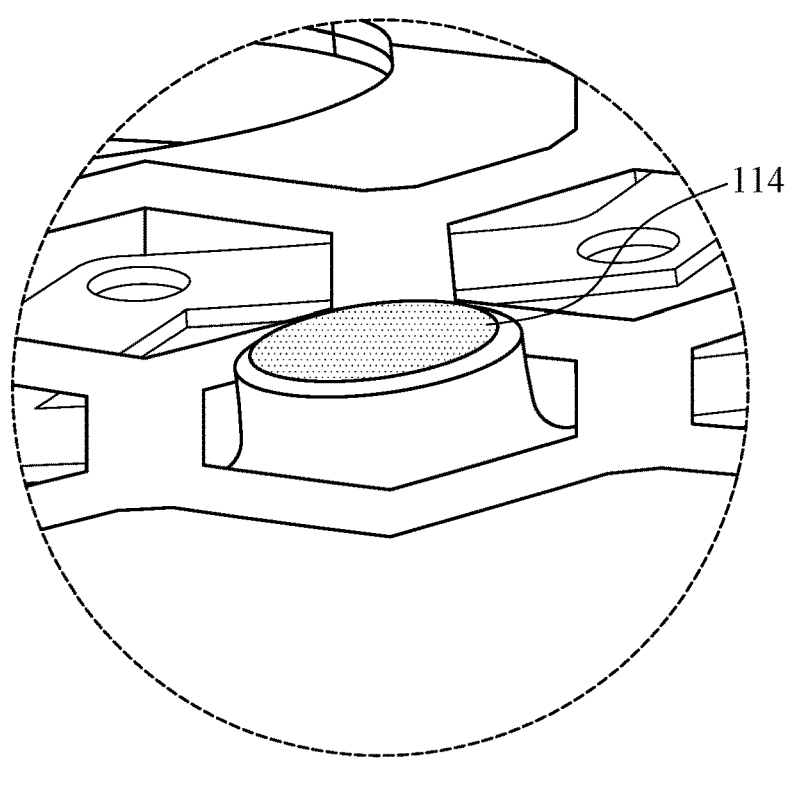
FIG. 4B illustrates a magnified view of a portion labeled as 4B in FIG. 4A.
FIG. 4C illustrates a magnified view of a portion labeled as 4C in FIG. 4A.

FIG. 4B illustrates a magnified view of a portion of the device 100 labeled as 4B in FIG. 4A. FIG. 4B illustrate the magnified view of the device 100, when the device 100 is not in use. The plurality of metal electrodes 114 as floating electrodes in that manner may be supported by elastic members at the points of attachment of the plurality of metal electrodes 114. In several embodiments of the invention, the elastic members may be made up of silicon. The elastic members allow the plurality of metal electrodes 114 to protrude upwards to a height greater than the height of the metallic layer 108. FIG. 4C illustrates a magnified view of a portion of the device 100 labeled as 4C in FIG. 4A. FIG. 4C illustrates the magnified view of the device 100, when the device 100 is in use. In FIG. 4C, the device 100 is making contact with the skin of the user, and the elastic members have been compressed to the height of metallic layer 108. Due to the elastic members and adaptability with the shape of the portion of the body, the plurality of metal electrodes 114 as floating electrodes provide relatively more comfortable effect on the portion of the body of the user. Moreover, the elastic members ensure that there is no direct contact between the plurality of light sources 112 and the skin of the user. For example, if the device 100 has been configured as a face mask, then the plurality of metal electrodes 114 as floating electrodes will provide relatively more comfortable effect on the face of the user and the elastic members and the transparent layer 106 will prevent direct contact of the plurality of light sources 112 and the facial skin of the user. This would prevent overheating and/or burning of the facial skin of the user.

Figure 5:
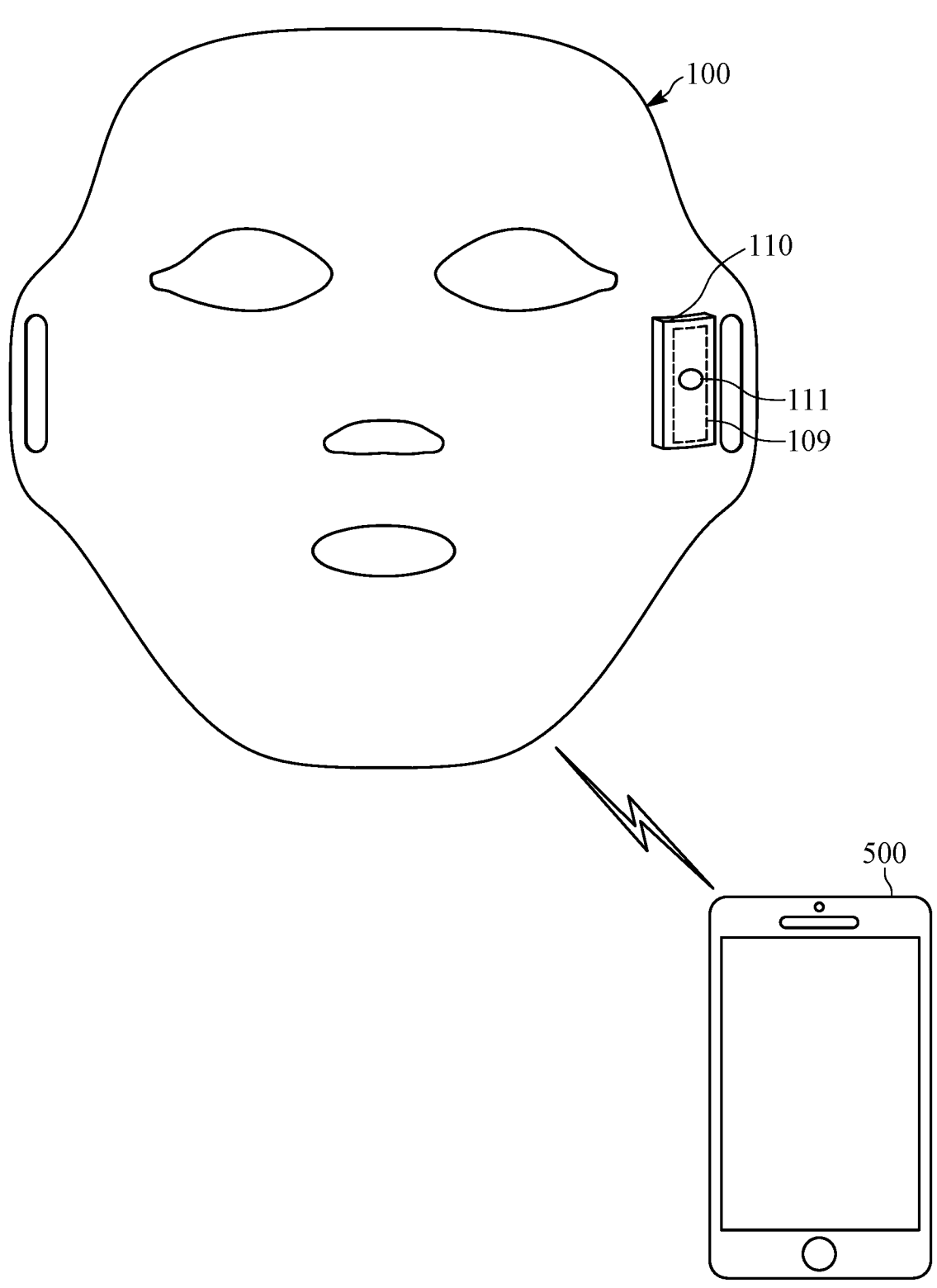
FIG. 5 illustrates the wearable phototherapy device connected with an external communication device, in accordance with an embodiment of the present invention.

FIG. 5 illustrates the device 100 connected with an external communication device 500, in accordance with an embodiment of the present invention. The device 100 includes a battery 109, a control unit 110, and a mode controller 111. The battery 109 may be a rechargeable battery, such as Nickel-Metal-Hydride, Lithium-ion or Lithium-polymer. The mode controller 111 may allow switching between several different therapies, such as Galvanic Therapy, TENS, EMS, and RF therapy. The control unit 110 includes a processor, a memory unit and a communication interface. The memory unit includes machine-readable instructions for the processor to execute. The communication with the external communication device 500 is routed through the communication interface. The control unit 110 is configured to connect with the external communication device 500 and receive an input. The input may correspond to switching between different therapies, such as TENS, EMS, RF and Galvanic Therapy, switching between continuous and pulse mode of operation of the LEDs or modification of emission characteristics of the plurality of LEDs such as wavelength of the irradiation.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to be providing the broadest scope consistent with the principles and the novel and inventive features disclosed or suggested herein. Accordingly, the invention is anticipated to hold on to all other such alternatives, modifications, and variations that fall within the scope of the present invention and appended claims.

The invention claimed is:

1. A wearable phototherapy device, the wearable phototherapy device comprising:
   an outer layer;
   an inner transparent silicone layer;
   a plurality of light sources located between the outer layer and the inner transparent silicone layer, wherein the plurality of light sources is directed towards the inner transparent silicone layer; and
   a metallic layer printed onto an inner surface of the inner transparent silicone layer, wherein the metallic layer is configured to conduct electrical current;
   wherein the inner transparent silicone layer includes a plurality of holes for the plurality of light sources and acts as a spacer between the metallic layer and the plurality of light sources.

2. The wearable phototherapy device as claimed in claim 1, further comprising a plurality of metal electrodes interspersed along the metallic layer.

3. The wearable phototherapy device as claimed in claim 2, wherein the plurality of metal electrodes are floating electrodes.

4. The wearable phototherapy device as claimed in claim 2, wherein the plurality of metal electrodes is configured to transmit electrical current within the metallic layer.

5. The wearable phototherapy device as claimed in claim 2, wherein a plurality of regions of the metallic layer between the interspersed plurality of metal electrodes correspond to a plurality of parts of the body of a user.

6. The wearable phototherapy device as claimed in claim 5, wherein the flow of current to the plurality of regions of the metallic layer is configured to be individually controlled through control of the flow of current to individual metal electrodes of the plurality of metal electrodes.

7. The wearable phototherapy device as claimed in claim 2, wherein the plurality of metal electrodes is configured to emit Radio-Frequency (RF) waves to provide RF treatment to the body of a user.

8. The wearable phototherapy device as claimed in claim 2, wherein the plurality of metal electrodes is supported by elastic members at the points of attachment of the plurality of metal electrodes.

9. The wearable phototherapy device as claimed in claim 1, wherein the wearable phototherapy device is in the shape of a face mask.

10. The wearable phototherapy device as claimed in claim 1, wherein the metallic layer has been provided in the form of a pattern including a plurality of connected hexagons.

11. The wearable phototherapy device as claimed in claim 1, wherein the plurality of light sources includes Light Emitting Diodes (LEDs).

12. The wearable phototherapy device as claimed in claim 1, wherein the plurality of light sources is configured to emit radiation in visible light and infrared wavelengths of the electromagnetic spectrum.

13. The wearable phototherapy device as claimed in claim 1, wherein the metallic layer is configured to conduct electrical current to provide Galvanic therapy to a user, the Galvanic therapy including desincrustation and iontophoresis.

14. The wearable phototherapy device as claimed in claim 1, wherein the metallic layer is configured to conduct electrical current to provide Transcutaneous Electrical Nerve Stimulation (TENS) to a user.

15. The wearable phototherapy device as claimed in claim 1, wherein the metallic layer is configured to conduct electrical current to provide Electronic Muscle Stimulation (EMS) to a user.

16. The wearable phototherapy device as claimed in claim 1, further comprising a battery, a control unit, and a mode controller.

17. The wearable phototherapy device as claimed in claim 16, wherein the control unit is configured to connect with an external communication device and receive an input from the external communication device.

18. The wearable phototherapy device as claimed in claim 2, wherein the plurality of metal electrodes are used to provide iontophoresis therapy.

19. The wearable phototherapy device as claimed in claim 2, wherein the plurality of metal electrodes are used to provide therapies including Electronic Muscle Stimulation (EMS), and Transcutaneous Electrical Nerve Stimulation (TENS).

* * * * *